United States Patent [19]
Heintze

[11] 4,347,749
[45] Sep. 7, 1982

[54] PRESS ROLLER CONTAMINATION MEASUREMENT

[76] Inventor: Hans U. Heintze, 1100 Dr. Penfield Ave., Apt. 512, Montreal, Canada, H3A 1A8

[21] Appl. No.: 228,189

[22] Filed: Jan. 26, 1981

[51] Int. Cl.³ ............................................. G01N 1/08
[52] U.S. Cl. ............................ 73/863.21; 73/864.33; 73/864.41; 73/864.51
[58] Field of Search ............... 73/150, 104, 864.33, 73/864.41, 864.51, 864.71, 864.72, 863.21

[56] References Cited

U.S. PATENT DOCUMENTS

| | | | |
|---|---|---|---|
| 2,826,077 | 3/1958 | Walker | 73/864.41 |
| 4,236,402 | 12/1980 | McGuire | 73/864.41 |
| 4,274,676 | 6/1981 | Chapel | 73/864.33 |

Primary Examiner—S. Clement Swisher

[57] ABSTRACT

An apparatus for measuring the foreign material deposited on a paper-contacting surface broadly comprising a frame member which is adapted to mate with the boundaries of and define an area on the surface within which the foreign material content is to be sampled, and additionally comprises a trough for contaminant collection.

The present invention also relates to a method of collecting a sample of contaminant from a paper-contacting surface comprising: isolating a minor portion of said surface, said portion having a bottom border, moving said contaminant from said portion across said bottom border and collecting said contaminant.

8 Claims, 3 Drawing Figures

PRESS ROLLER CONTAMINATION MEASUREMENT

FIELD OF THE INVENTION

The present invention relates to a means for the collection of samples of deposits of contaminants on paper contacting surfaces. More particularly, the present invention relates to a method and apparatus for collecting samples of foreign material from printing surfaces, for the purposes of measurement and/or testing.

BACKGROUND OF THE INVENTION/PRIOR ART

During the process of offset or dilitho printing, it is a common occurrence for paper fibres, coating, mineral fillers, etc. to be detached from the paper being printed, and for such foreign material to be deposited on or adhere to the printing surface of the press. While this detachment of paper constituents and their deposition on the press results principally from the combined effects of the passage of the paper through the nip under pressure and the tacky inks employed in such printing, it has a deleterious effect on the press performance as manifested by a decrease in the printing plate life and the quality of the copies produced. Similar deposits and accumulation of paper fibres can be formed on dryer cans or calender rolls. While these deposits may be any or all of the paper components indicated above, they will for convenience' sake, be referred to in the following discussion as lint.

Techniques which are currently used to measure the lint on offset printing presses, in order to test the linting properties of papers, are relatively crude and time-consuming. One such method entails the removal and washing of the whole blanket in order to collect the lint sample. Another method is to utilize a sticky-tape eg. a tape with a pressure-sensitive adhesive and to apply it against the surface of the blanket and cause the superficial lint to adhere to the tape, thereby yielding a subjective indication of the lint deposited. This is often misleading as to the linting propensity of the web since only a part of the lint is collected, and furthermore because the linting propensity is estimated visually. The application of this method is restricted to low lint levels, since individual lint fibres have to be counted by eye, and a high density of lint does not permit an accurate count, due to the presence of fibre clusters. The results obtained by this method often vary with the person making the measurement; and additionally their interpretation is ambiguous. While such procedures have been commonly employed for a long time, no simple and efficient lint sampling technique capable of yielding quantitative and objective results has as yet been evolved.

It is therefore the object of this invention to provide a method and apparatus for collecting representative lint samples for measurement and/or testing.

BRIEF DESCRIPTION OF THE INVENTION

In one aspect, the present invention relates to an apparatus for the measurement of deposits of foreign material on a paper-contacting surface comprising: a frame member adapted to mate with the surface and define a predetermined area from which the contaminant is to be substantially completely removed, a doctor's edge forming at least a significant portion of the bottom boundary of the area, a trough positioned to receive the material passing over the doctor's edge.

In another aspect, the present invention also relates to the method of collecting a sample of contaminant from a paper-contacting surface comprising: isolating a minor portion of said surface, said portion having a bottom border, moving said contaminant from said portion across said bottom border and collecting said contaminant.

DETAILED DESCRIPTION OF THE PREFERRED EMBODIMENT

Accordingly, the present invention relates to an apparatus and a method for collecting a sample of the press contaminant (lint) content of a paper contacting surface e.g. a printing surface such as a blanket of an offset printing press which has deposits of paper derived foreign material.

Figure 1:
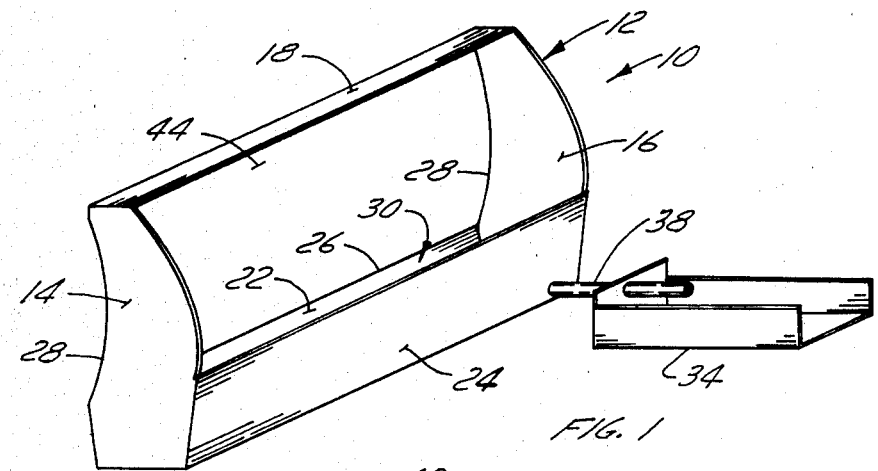
FIG. 1 is a schematic isometric view of the lint collector of the present invention.
Figure 2:
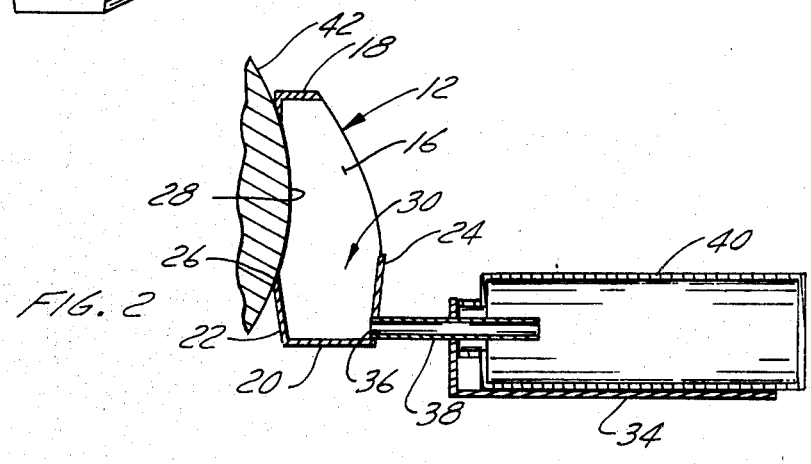
FIG. 2 is a horizontal section through the lint collector of FIG. 1.

As shown in the accompanying FIGS. 1 and 2, the lint collector 10 is composed of a frame generally indicated at 12 having side walls 14 and 16, a top wall 18 and a bottom wall 22. The bottom wall 22 is provided with a doctor's edge 26 which is adapted to contact the surface. The leading edges of the frame 12, including the top wall 18, the doctor's edge 26 on bottom wall 22 and particularly the leading edges of side walls 14 and 16 are curved as indicated at 28 so as to mate with the curved surface of the blanket or roller and seal off the area from which the lint sample is to be taken. The seal may equivalently be achieved by the use of a rubber seal around the frame where it is adapted to contact the surface thereby facilitating use of the device on rollers of different curvature.

The frame 12 is provided with a trough indicated at 30. The trough is provided with a rear wall 24, a bottom wall 20 and a pair of end walls 14 and 16 which are extensions of the side walls of the frame 12. The front wall of the trough is formed by the bottom wall 22 of the frame 12 and terminates at the upper end of the doctor's edge 26. Preferably, at the back 24 at one end thereof will be provided a tray generally indicated at 34 and an aperture 36 will be provided through the wall 24, leading to the tray 34. Preferably, the aperture 36 will be at a lower corner of the trough 30 so as to facilitate the removal of the liquid containing the lint from the trough. The collecting bottle 40, which is illustrated in FIG. 2 communicates with the trough 30 via the aperture 36 and the connecting tube 38 which projects rearwardly from the aperture 36 and is retained in the tray 34 to collect the sample that passes into the trough 26. The dimensions of the tray 34 can be chosen so as to permit the use of the tray as a handle when using the apparatus.

This apparatus can be used to isolate an area of the surface, preferably with the doctor blade defining the bottom border and moving the lint from the area over the doctor blade and collecting the lint. In operation, the unit 10 is held tightly against the surface from which the lint sample is to be obtained. For the purposes of comparison, successive lint samples should be taken in the areas having the same print. Taking lint samples resulting from the use of the same ink and print but derived from different papers will allow the comparison of linting propensities of the various papers. This is illustrated in the embodiment illustrated in FIG. 2 and comprises a roll generally indicated at 42, so that the frame 12 blocks off an area generally indicated at 44 in FIG. 1. i.e. between the side walls 14 and 16, the top wall 18 and the doctor's edge 26. With the lint collector 10, so placed against the roll, a lint removing means which is described below in greater detail, is employed to dislodge the lint from this area and move it from the area 44 into the trough 30. This lint material, after the area 44 has been cleaned, may then be poured into the collecting bottle 40 through the aperature 36 in the back wall 24 via the connecting tube 38 by tilting the unit 10. Thereafter, the lint material in the sample collected in the bottle 40 may be separated from the wash liquid for further testing and/or characterization of the lint on the surface.

Figure 3:
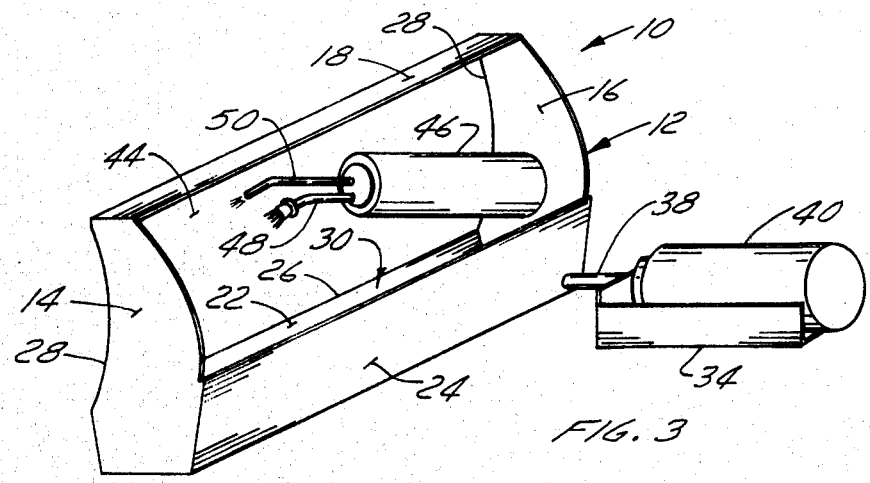
FIG. 3 is a schematic isometric view of the lint collector in conjunction with the lint-removing means.

The lint removing means which is to be employed in conjunction with the frame member 12 in moving the lint sample from the area 44 to the trough 30, will usually comprise a liquid dispensing means, eg. a wash bottle. The liquid dispensing means will preferably be integrally provided with means for mechanically dislodging lint, which can for example be a "squeegee" (of appropriate hardness rubber such that it will not mechanically damage the blanket), a brush or a blade. A particularly efficacious arrangement of this lint removing means is a wash bottle provided with a brush attached to it with the working end of the brush terminating adjacent the liquid dispensing end of the wash bottle. This structure is useful in that it permits an user to position the frame with one hand and remove the lint with the other. FIG. 3 further illustrates the use of this apparatus on a roll of an offset printing press. The unit 10 is applied to roll (42) with one hand and isolates an area (44). In a preferred embodiment a squeeze bottle 46 having a brush 48 and a liquid spray nozzle 50 are manipulated with the other hand. The wash liquid can be either water only, petroleum ether, water-alcohol (eg. isopropanol), or water-detergent combinations. The preferred wash liquid is one which easily wets the rubber blanket and does not damage any of the press components. The wash liquid is sprayed onto the area 44 and with the aid of the brush 48, as complete a removal of lint as is possible is carried out. The lint contained in the liquid goes over the doctor blade 26, into the trough 30 from which it can be poured into bottle 40 via aperture 36 and the tube 38. The trough can then be washed out with the liquid to remove all traces of the lint which will also be collected in the bottle. The procedure permits the collection of a lint sample from a predetermined area, for the purposes of characterization and for testing of the lint, for example, with regard to its weight, shape, size, size distribution and chemical nature.

As will be readily evident from the preceding description, the apparatus described therein provides a convenient and rapid means for the collection of a lint sample from a surface and the characterization thereof. The present invention decreases the degree of operator-dependence of the results, which was one of the major drawbacks of the techniques which were previously employed e.g. the procedure which used a pressure sensitive adhesive tape.

The invention described above can be subjected to a great variety of modifications which will be evident to those skilled in the art, and which fall within the scope of the appended claims.

I claim:

1. An apparatus for the measurement of the content of contaminant on a paper-contacting surface comprising a frame member adapted to mate with the surface and define a predetermined area from which said contaminant is to be substantially completely removed, a doctor's edge forming at least a significant portion of the bottom boundary of the area, a trough positioned to receive the material passing over the doctor's edge.

2. Apparatus as defined in claim 1 additionally comprising a collection means communicating with said trough.

3. Apparatus as defined in claim 2 wherein said collection means is mounted in a handle for grasping said apparatus.

4. Apparatus as defined in claims 1, 2 or 3 additionally comprising a wash liquid dispensing means having a means for dislodging said contaminant from the surface, projecting therefrom.

5. Method for the collection of a sample of contaminant from a paper-contacting surface comprising isolating a minor portion of said surface, said portion having a bottom border, moving said contaminant from said portion across said bottom border and collecting said contaminant.

6. Method as defined in claim 5, wherein said moving of said contaminant is carried out by washing said portion of said surface with a liquid.

7. Method as defined in claim 6, comprising the additional step of separating said contaminant from said liquid.

8. Method as defined in claims 6 or 7 where said liquid is chosen from the group consisting of water, petroleum ether, water-alcohol, and water-surfactant combinations.

* * * * *